(12) United States Patent
Navon et al.

(10) Patent No.: US 10,736,973 B2
(45) Date of Patent: Aug. 11, 2020

(54) GLUCOSE ANALOGS FOR DIAGNOSIS STATES

(71) Applicant: TECHNOLOGY INNOVATION MOMENTUM FUND (ISRAEL) LIMITED PARTNERSHIP, Tel Aviv (IL)

(72) Inventors: Gil Navon, Tel Aviv (IL); Michal Rivlin, Hod Hasharon (IL); Ilan Tsarfaty, Tel Aviv (IL)

(73) Assignee: TECHNOLOGY INNOVATION MOMENTUM FUND (ISRAEL) LIMITED PARTNERSHIP, Tel Aviv (IL)

( * ) Notice: Subject to any disclaimer, the term of this patent is extended or adjusted under 35 U.S.C. 154(b) by 40 days.

(21) Appl. No.: 15/129,255

(22) PCT Filed: Mar. 26, 2015

(86) PCT No.: PCT/IL2015/050327
§ 371 (c)(1),
(2) Date: Sep. 26, 2016

(87) PCT Pub. No.: WO2015/145447
PCT Pub. Date: Oct. 1, 2015

(65) Prior Publication Data
US 2018/0177898 A1   Jun. 28, 2018

Related U.S. Application Data

(60) Provisional application No. 61/971,171, filed on Mar. 27, 2014.

(51) Int. Cl.
*A61K 49/10* (2006.01)
(52) U.S. Cl.
CPC .................... *A61K 49/10* (2013.01)
(58) Field of Classification Search
CPC ................ A61K 49/00; A61K 49/10
USPC .......... 424/1.11, 1.65, 1.73, 1.81, 1.85, 1.89, 424/9.1, 9.2, 9.3, 9.4
See application file for complete search history.

(56) References Cited

U.S. PATENT DOCUMENTS

| | | | | |
|---|---|---|---|---|
| 7,001,888 B2 * | 2/2006 | Tidmarsh | ............ | A61K 47/549 514/23 |
| 7,560,230 B2 * | 7/2009 | Tidmarsh | ............ | C12Q 1/6886 435/6.11 |
| 2006/0172305 A1 * | 8/2006 | Tidmarsh | ............ | C12Q 1/6886 435/6.11 |
| 2011/0152671 A1 | 6/2011 | Aime et al. | | |
| 2012/0019245 A1 | 1/2012 | Reddy et al. | | |

FOREIGN PATENT DOCUMENTS

| | | |
|---|---|---|
| CN | 102132169 A | 7/2011 |
| WO | 2012/082874 A2 | 6/2012 |

OTHER PUBLICATIONS

Goodpaster et al, Diabetes, published online on Feb. 13, 2014, vol. 63, pp. 1058-1068. (Year: 2014).*
Rivlin et al, Scientific Reports, 3:3045, pp. 1-7. (Year: 2013).*
Goodpaster et al, Diabetes, published online on Feb. 13, 2014, vol. 63, No. 3, pp. 1058-1068 (Year: 2014).*
Bertoldo et al, Diabetes, vol. 55, pp. 3028-3037 (Year: 2006).*
Goodpaster et al, Diabetes, published online on Nov. 12, 2013, pp. 1-41 (Year: 2013).*
Rempel et al, FEBS Letters, vol. 385, pp. 233-237 (Year: 1996).*
Nakagawa et al, Endocrine Journal, published online on Nov. 7, 2013, vol. 61, No. 2, pp. 119-131 (Year: 2013).*
Walker-Samuel et al, Nature Medicine, published online on Jul. 7, 2013, pp. 1-7 (Year: 2013).*
Akhtari et al., "Functionalized Magnetonanoparticles in Visualization of Intracranial Tumors on MRI", Mol Imaging Biol, vol. 15, No. 3, pp. 299-306, (2013).
Chan et al., "Natural D-glucose as a Biodegradable MRI Contrast Agent for Detecting Cancer", Magnetic Resonance in Medicine, vol. 68, No. 6, pp. 1764-1773, (2012).
Goodpaster et al., "Interactions among Glucose Delivery, Transport, and Phosphorylation That Underlie Skeletal Muscle Insulin Resistance in Obesity and Type 2 Diabetes: Studies With Dynamic PET Imaging", Diabetes, vol. 63, No. 3, pp. 1058-1068, (2014).
Heiss et al., "Demonstration of Decreased Functional Activity of Visual Cortex by [11C]Methylglucose and Positron Emission Tomography", Neuroradiology, vol. 23, No. 1, pp. 45-47, (1982).
Rivlin et al., "Molecular imaging of tumors and metastates using chemical exchange saturation transfer (CEST) MRI", Scientific Reports, vol. 3, pp. 1-7, (2013).
Rivlin et al., "Functional Molecular Imaging of Tumors by Chemical Exchange Staturation Transfer MRI of 3-O-Methyl-D-Glucose", Magnetic Resonance in Medicine, vol. 72, No. 5, pp. 1375-1380, (2014).
Salem et al., "PET imaging of hepatocellular carcinoma with 2-deoxy-2[18F]fluoro-D-glucose, 6-deoxy-6[18F]fluoro-D-glucose, [1-11C]-acetate and [N-methyl-11C]-choline", Q J Nucl Med Mol Imaging, vol. 53 No. 2, pp. 144-156, (2009).
Waki et al., "Glucose Transporter Protein-Independent Tumor Cell Accumulation of Fluorine-18-AFDG, a Lipophilic Fluorine-18-FDG Analog", J Nucl Med, vol. 39, No. 2, pp. 245-250, (1998).
Walker-Samuel et al., "In vivo imaging of glucose uptake and metabolism in tumors", Nature Medicine, vol. 19, No. 8, pp. 1067-1072, (2013).
Zaman et al., "12212—Atherosclerotic Plaque Detection With a Fluorescence/Radionuclide Intravascular Imaging System for 18F-FEG and 6-NBDG", Circulation, vol. 128, No. 22, Suppl. S, (2013).
The International Search Report for PCT/IL2015/050327, four pages, dated Sep. 25, 2015.
Czernin et al., "PET/CT imaging: The incremental value of assessing the glucose metabolic phenotype and the structure of cancers in a single examination", European Journal of Radiology, 2010, vol. 73, pp. 470-480.

(Continued)

*Primary Examiner* — D. L. Jones
(74) *Attorney, Agent, or Firm* — Vorys, Sater, Seymour and Pease LLP

(57) ABSTRACT

Provided are methods and formulations for imaging at least one body region of a subject, employing a glucose analog resistant or inactive to phosphrylation, or which is not a substrate for hexokinase.

13 Claims, 4 Drawing Sheets

(56) References Cited

OTHER PUBLICATIONS

Schuit, "Is GLUT2 required for glucose sensing?", Diabetologia, 1997, vol. 40, pp. 104-111.

* cited by examiner

GLUCOSE ANALOGS FOR DIAGNOSIS STATES

TECHNOLOGICAL FIELD

The invention generally provides a novel use of a family of glucose analogs for diagnosis of disease states in a subject.

BACKGROUND OF THE INVENTION

Glucose and its analogues 2-deoxy-D-glucose (2-DG) and 2-fluoro-deoxy-D-glucose (FDG) are known to be taken up preferentially by cancer cells, a phenomenon that is known as the "Warburg effect". The positron emission tomography (PET) method makes use of this phenomenon by imaging FDG containing the radioactive fluorine atom $^{18}$F. The chemical exchange saturation transfer (CEST) NMR method enables to detect low concentrations of metabolites that contain residues with exchangeable protons such amine, amide or hydroxyl. The enhanced sensitivity of the method allows obtaining images of relatively low concentrations of endogenous cellular components or exogenous agents by MRI.

US 2012/0019245 [1] discloses using CEST MRI to monitor the concentration of various neurotransmitters and energy metabolites to characterize and monitor various disease states in the body, more specifically in the liver, brain and myocardium, correlated to the concentration of that metabolized.

Detection of administered sugar can employ CEST MRI due to the presence of the exchangeable protons in said sugar. WO 2012/082874 [2] discloses methods for MRI for the detection of tissue physiological parameters in a subject by using non-labeled sugar to recognize whether at least one tissue-related parameter is abnormal.

Recently, the CEST MRI method has been shown to enable the imaging of glucose and its analogues with enhanced sensitivity and these compounds were suggested to be used for cancer diagnosis [3,4]. However glucose gives inferior CEST signal due to its rapid conversion to lactic acid by glycolysis, and the two analogues 2-DG and FDG that undergo phosphorylation but do not undergo further metabolism are toxic at high concentrations such as 3 g/kg for 2-DG in rats.

REFERENCES

[1] US 2012/0019245
[2] WO 2012/082874
[3] Rivlin M. et al., (2013), *Scientific Report* 3: 1-7
[4] Rivlin M. et al., (2014), *Magn. Reson. Med* 72:1375-1380

GENERAL DESCRIPTION

In accordance with the technology disclosed in the present application, sugar analogs, e.g., 3-O-methyl glucose (3OMG) are employed for imaging tissue abnormalities. The results presented herein demonstrate that the methods of the invention are potential replacements of PET/CT or PET/MRI in the clinic for the detection of tissue abnormalities such as tumors and metastases, distinguishing between malignant and benign tumors and monitoring tumor response to therapy, without the need for radio-labeled isotopes.

The family of sugar analogs, used in accordance with the invention, may be defined as nontoxic non-metabolizable derivatives of glucose, which have been demonstrated to be taken-up rapidly and preferentially by abnormalities such as tumors. Unlike glucose and other glucose analogs, 3OMG, as an exemplary candidate imaging agent according to the invention, does not serve as substrate for hexokinase, consequently does not undergo phosphorylation and is entirely excreted by the kidneys.

Thus, the invention provides use of at least one glucose analog, being oxidative phosphorylation inactive, in a method of imaging at least one tissue abnormality. The imaging may be utilized for the purpose of detecting, diagnosing or monitoring a disease state, as further explained herein below.

In one aspect the invention provides a method for diagnosis of a disease or disorder in a subject, said method comprising administering to the subject a diagnostically effective amount of at least one glucose analog, and imaging the subject or a body region of the subject to thereby identify body regions in which said analog has been localized, said glucose analog being oxidative phosphorylation inactive.

In some embodiments, the method of the invention is employed for determining the site of disease and/or for distinguishing between healthy and abnormal tissues or organs. In some embodiments, the method is used for distinguishing or differentiating between malignant and benign tumors.

By another aspect the invention provides a method for diagnosis of a disease or disorder in a subject, said method comprising administering to the subject a diagnostically effective amount of at least one glucose analog, and imaging the subject or a body region of the subject to thereby identify body regions in which said analog has been localized, said analog being selected from phosphorylation-resistant glucose analogs and analogs which are not substrates for hexokinase.

As used herein, the body region refers to the whole body, any part of the body, any one or more regions of the body or any tissue or organ.

The glucose analogs are selected amongst such which are resistant to glycolysis and oxidative phosphorylation. In other words, the glucose analogs are selected to be resistant to degradation or phosphorylation by any one or more metabolic pathways leading to a transformation in the structure and/or activity of the glucose analog.

The glucose analogs employed in accordance with the invention are additionally or alternatively selected from such analogs which are not substrates to hexokinase enzyme or enzymes that phosphorylate hexoses.

The glucose analogs so characterized may be selected amongst $C_1$-$C_5$—O-alkylated glucose and glucose-$C_1$-$C_5$-alkanoates. In some embodiments, the glucose analog is selected from $C_1$-$C_5$—O-alkylated glucose. The $C_1$-$C_5$—O-alkylated glucose may have the alkyl group at any oxygen of the glucose; namely, the alkylated glucose may be selected from $C_1$-$C_5$-1-O-alkylated glucose, $C_1$-$C_5$-2-O-alkylated glucose, $C_1$-$C_5$-3-O-alkylated glucose, $C_1$-$C_5$-4-O-alkylated glucose and $C_1$-$C_5$-6-O-alkylated glucose.

As used herein, "$C_1$-$C_5$—O-alkylated glucose" refers to a glucose wherein at least one of its oxygen atoms is alkylated (—O-alkylated glucose) by an organic moiety having between 1 and 5 carbon atoms ($C_1$-$C_5$—O-alkylated); the organic moiety being typically an aliphatic group (e.g., comprising carbon and hydrogen atoms, each carbon atom being sp$^3$ hybridized), which optionally may be substituted by a group, e.g., selected from —H, a halide (F, Br, Cl, or I), —OH, —NO$_2$, —NH$_2$, secondary or tertiary amines, ethers, esters, and others. In some embodiments, the aliphatic group containing between 1 and 5 carbon atoms may be selected, inter alia and without limitation, from methyl, ethyl, propyl, butyl, pentyl groups, and any structural isomer thereof.

In some embodiments, the C$_1$-C$_5$—O-alkylated glucose is selected from methyl-O-glucose, ethyl-O-glucose, propyl-O-glucose, iso-propyl-O-glucose, propyl-O-glucose, sec-butyl-O-glucose, t-butyl-O-glucose, n-butyl-O-glucose and n-pentyl-O-glucose. The substitution of the alkyl or alkanoate groups may be on any one or more of the oxygen atoms at positions 1, 2, 3, 4 and/or 6 of a glucose ring. Thus, each of these alkylated compounds may be selected from 1-O-glucose, 2-O-glucose, 3-O-glucose, 4-O-glucose and 6-O-glucose (for example: 1-O-glucose alkylated compound is a glucose analog having its oxygen at position 1 alkylated, as defined).

In other words, where, for example, the C$_1$-C$_5$—O-alkylated glucose is a methyl-O-glucose, it may be selected from 1-O-methylglucose, 2-O-methylglucose, 3-O-methylglucose, 4-O-methylglucose and 6-O-methylglucose.

In some embodiments, the C$_1$-C$_5$—O-alkylated glucose is selected amongst C$_1$-C$_5$-3-O-alkylated glucose analogues, e.g., 3-O-methylglucose, 3-O-ethylglucose, 3-O-propylglucose, 3-O-iso-propylglucose, 3-O-n-butylglucose, 3-O-sec-butylglucose, 3-O-t-butylglucose, and 3-O n-pentylglucose. For the sake of clarity, the above listed glucose analogs may have alternative nomenclatures. For example, methyl-3-O-glucose may also be referred to as 3-O-methylglucose. Other analogs may have similar nomenclature.

In some embodiments, the C$_1$-C$_5$-3-O-alkylated glucose is 3-O-methylglucose (3OMG).

Alternatively, in some embodiments, the glucose analog is selected from glucose-C$_1$-C$_5$-alkanoate. In some embodiments, the glucose-C$_1$-C$_5$-alkanoate is selected from 1-O-glucose-C$_1$-C$_5$-alkanoate, 2-O-glucose-C$_1$-C$_5$-alkanoate, 3-O-glucose-C$_1$-C$_5$-alkanoate, 4-O-glucose-C$_1$-C$_5$-alkanoate and 6-O-glucose-C$_1$-C$_5$-alkanoate.

In some embodiments, the glucose-C$_1$-C$_5$-alkanoate is selected from O-glucose-acetate, O-glucose-ethanoate, O-glucose-propanoate, O-glucose-iso-propanoate, O-glucose-sec-butanoate, O-glucose-t-butanoate, O-glucose-butanoate and O-glucose-pentanoate.

In some embodiments, the glucose-C$_1$-C$_5$-alkanoate is 3-O-glucose acetate.

The methods, uses and compositions or formulations, or kits according to the invention may utilize one or more of said at least one glucose analogs. The selection of the specific analog and the determination of whether and which one or more analogs should be used in combination, may be determined by a medical practitioner based, inter alia, on subject-related considerations and/or therapy-related considerations, such as the subject to be treated (age, sex, etc), the subject's general health, the disease type to be imaged, the region of the subject's body to be imaged, the characterization of the imaging period, the duration of imaging, and others.

Thus, the glucose analogs may be utilized for imaging (e.g., for the purpose of monitoring) a disease state, determining severity of a disease state, determining effectiveness of treatment, and others.

Therefore, the invention further contemplates, in another of its aspects, a method for monitoring a disease state in a subject, the method comprising administering to said subject at least one glucose analog, imaging the subject's body or region thereof to obtain at least one imaging parameter indicative of the disease or disorder state, and comparing said at least one imaging parameter to at least one parameter obtained from said subject at an earlier point in time or upon identification of at least one symptom associated with said disease or disorder, wherein the comparison permits determining the progression of the disease or disorder state.

In some embodiments, "monitoring" involves obtaining multiple parameters indicative of a disease state and progression at various points in time, prior to, during or after commencement of treatment, and comparing the collected data to determine any one therapeutic parameter. The monitoring may be conducted over a period of time, for example every few days or weeks, once a week, once a month, at the onset of treatment and at any time thereafter, etc.

The "imaging parameter" may be any measurable parameter which can be obtained using any imaging technique available, to be applied to a subject's body or to any part of the body. Examples of such parameters include, inter alia, images (e.g. four-dimensional images or pictures of functional processes in the body) acquired by a nuclear medicine technician, magnetic resonance imaging (MRI), positron emission tomography (PET), radiology (X-ray), ultrasound, computed tomography (CT) or fluorescent imaging.

In some embodiments, monitoring the levels of at least one imaging parameter in the subject, in accordance with any one methods of the invention, may also assist in screening for likely candidates for treatment of a disease or a disease state.

The monitoring may be conducted by any imaging technique or any a diagnostic method. In some embodiments, the monitoring is conducted by pulse sequence of gradient echo. In other embodiments, the monitoring is conducted by MRI pulse sequences, enabling to measure changes in tumor's metabolism as a result of exposure to a glucose derivative. In further embodiments, the monitoring is conducted by EPI (echo planar imaging), Spin echo (RARE) or any other pulse sequence that yields high resolution image contrast.

In a further aspect, the invention provides a method for determining the severity of a disease or disorder in a subject, the method comprising administering to said subject at least one glucose analog, imaging the subject's body or region thereof to obtain at least one imaging parameter (e.g., indicative of the state of the disease or disorder), and comparing said at least one imaging parameter to at least one parameter obtained from said subject at the onset of treatment or prior to treatment commencement, wherein the comparison permits determining the severity of the disease or disorder in the subject.

In another aspect the invention provides a method for determining the effectiveness of a therapeutic treatment of a disease or disorder in a subject, the method comprising administering to said subject at least one glucose analog, imaging the subject's body or region thereof to obtain at least one imaging parameter (e.g., indicative of the state of the disease or disorder), and comparing said at least one imaging parameter to at least one parameter obtained from said subject at the onset of treatment or prior to treatment commencement, wherein the comparison permits determining the effectiveness of the therapeutic treatment of the disease or disorder in the subject.

The determination of the effectiveness of treatment may be achieved at the end of treatment or at any point in time during the treatment period. Generally, and depending on the disease and disease state, the effectiveness is indicated by any one or more changes in the disease state or any symptom associated therewith, such as decreased proliferation.

In some embodiments, the aforementioned methods of the invention are used for evaluating the effectiveness of drug treatment in cancer treatment, for example, in evaluating the ability of a drug to reduce the size of a tumor or to prevent the tumor from growing, wherein the method comprises imaging the tumor with an imaging agent selected from the herein disclosed glucose analogs and measuring the size of the tumor; administering the drug to the subject to affect at least one of reduction in the size of the tumor and prevention of growth of the tumor; re-imaging the tumor with the same or different glucose analog and measuring the size of the tumor, and comparing the size of tumor after administration of the drug to the size of the tumor prior to administration of the drug.

The glucose analogs are employed effectively in imaging "a disease or disorder" in a subject; the disease or disorder being any disease or disorder that involves a high rate of glycolysis in a tissue region as compared to other neighboring or vicinal tissue regions. In some embodiments, the disease or disorder is selected from proliferative disease or disorders. The "proliferative disease disorders" are typically selected amongst diseases characterized by abnormal cell proliferation.

In some embodiments, the proliferative disease or disorder is cancer. As used herein the term "cancer" relates to a neoplastic disease which is characterized by abnormal and uncontrolled cell division causing malignant growth or tumor. Cancer includes the two broad categories of carcinoma and sarcoma.

In some embodiments, the cancer is selected amongst cancerous states of skin tissues, organs, blood and blood vessels, which include cancers of the bladder, bone, blood, brain, breast, cervix, chest, colon, endrometrium, esophagus, eye, head, kidney, liver, lymph node, lung, mouth, neck, ovary, pancreas, prostate, rectum, stomach, testicles, throat or uterus.

In some embodiments, the cancer is a solid tumor or tumor metastasis.

In a further embodiment of the present invention, said cancer may be selected from, however not limited to, the group consisting of lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, glioblastoma, benign tumor of the skin (e.g. keratoacanthomas), breast carcinoma (e.g. advanced breast cancer), kidney carcinoma, ovary carcinoma, bladder carcinoma and epidermal carcinoma.

In some embodiments, the cancer includes, but is not particularly limited to, advanced malignancy, amyloidosis, neuroblastoma, meningioma, hemangiopericytoma, multiple brain metastase, glioblastoma multiformis, glioblastoma, brain stem glioma, poor prognosis malignant brain tumor, malignant glioma, recurrent malignant glioma, anaplastic astrocytoma, anaplastic oligodendroglioma, neuroendocrine tumor, adenocarcinoma, Dukes C & D colorectal cancer, unresectable colorectal cancer, metastatic hepatocellular carcinoma, Kaposi's sarcoma, karotype acute myeloblastic leukemia, Hodgkin's lymphoma, Non-Hodgkin's lymphoma, cutaneous T-cell lymphoma, cutaneous B-cell lymphoma, diffuse large B-Cell lymphoma, low grade follicular lymphoma, malignant melanoma, malignant mesothelioma, malignant pleural effusion mesothelioma syndrome, intraperitoneal carcinoma, papillary serous carcinoma, gynecologic sarcoma, soft tissue sarcoma, scelroderma, subcutaneous vasculitis, Langerhans' cell histiocytosis, leiomyosarcoma, fibrodysplasia ossificans progressive, hormone refractory prostate cancer, resected high-risk soft tissue sarcoma, unrescectable hepatocellular carcinoma, Waldenstroms macroglobulinemia, smoldering myeloma, indolent myeloma, salpinx cancer, androgen-dependent prostate cancer, androgen-dependent stage IV non-metastatic prostate cancer, hormone-insensitive prostate cancer, chemotherapeutic-insensitive prostate cancer, papillary thyroid carcinoma, follicular thyroid carcinoma, medullary thyroid carcinoma, and leiomyoma, and head and neck cancer.

The disorder to be imaged may alternatively be wounds and atherosclerotic plaques.

The subject to be diagnosed may be one suffering from the disease to be monitored or one having predisposition to suffer from said disease or disorder or one having symptoms associated with the disease or disorder or one suspecting to suffer from said disease or disorder.

For successful imaging, the glucose analogue should be administered in a "diagnostically effective amount", namely in an amount which would allow for an efficient molecular imaging under the conditions relevant to the type of the imaging technique (e.g. PET, CEST etc) used, the acquisition parameters of the specific imaging technique used, the area of the body imaged, the physical condition of the subject, the purpose of the test or any other factors which are apparent to the person skilled in art.

The diagnostically effective amount may vary depending on the glucose analog used, the age, weight, and clinical condition of the recipient patient, and the experience and judgment of the clinician or practitioner administering the diagnostic analog, among other factors affecting the selected dosage.

The glucose analogs may be administered by any medically acceptable means suitable for administering pharmaceutical compositions, including oral, rectal, vaginal, nasal, topical, transdermal, and parenteral (including subcutaneous, intramuscular, intrasynovial, intraperitoneal, intradermal and intravenous) administrations.

In some embodiments, the sugar analogs may be administered orally as a diagnostically pre-formulated composition.

The imaging of the body or body region following administration of the glucose analogue may be by an imaging technique selected from magnetic resonance imaging (MRI), positron emission tomography (PET), radiology (X-ray), ultrasound, computed tomography (CT), fluorescent imaging, and may additionally be useful in angiography, plethysmography, lymphography and mammography.

In some embodiments, the imaging technique is MRI.

In some embodiments, the MRI technique is selected from chemical exchange saturation transfer (CEST) MRI, diffusion MRI, magnetic resonance angiography, dynamic contrast-enhanced MRI (DCE) MRI, and positron emission tomography (PET). In some embodiments, said MRI is chemical exchange saturation transfer (CEST) MRI.

In another aspect, the invention provides a kit for diagnostic use, the kit comprising at least one glucose analog as recited herein or a formulation comprising said analog; and instructions for use.

The invention further contemplates a diagnostic formulation comprising at least one glucose analog, as defined herein, and at least one diagnostically acceptable carrier. In some embodiments, the formulation is suitable for administration to a subject in preparation for imaging by a technique as disclosed herein, e.g., MRI.

The invention further provides use of at least one glucose analog, as defined herein, for the preparation of a diagnostic formulation.

The invention is further directed to a glucose analog, as defined, for use as an imaging agent for detecting thereof in a body of a subject following administration thereof.

The invention further provides a combination of at least one glucose analog, as defined, with at least one additional imaging agent, for uses detailed herein.

In some embodiments, the method of imaging according to the invention is for diagnosis of a disease or disorder in a subject, said method comprising administering to the subject a diagnostically effective amount of at least one glucose analog, and imaging the subject or a body region of the subject to thereby identify body regions in which said analog has been localized, said glucose analog being oxidative phosphorylation inactive.

In some embodiments, the method is for determining the site of disease and/or for distinguishing between healthy and abnormal tissues or organs. The method may alternatively be utilized for distinguishing or differentiating between malignant and benign tumors.

The invention further provides a method for diagnosis of a disease or disorder in a subject, said method comprising administering to the subject a diagnostically effective amount of at least one glucose analog, and imaging the subject or a body region of the subject to thereby identify body regions in which said analog has been localized, said analog being selected from phosphorylation-resistant glucose analogs and analogs which are not substrates for hexokinase.

The invention further provides a method for monitoring a disease state in a subject, the method comprising administering to said subject at least one glucose analog, imaging the subject's body or region thereof to obtain at least one imaging parameter indicative of the disease or disorder state, and comparing said at least one imaging parameter to at least one parameter obtained from said subject at an earlier point in time or upon identification of at least one symptom associated with said disease or disorder, wherein the comparison permits determining the progression of the disease or disorder state.

The invention further provides a method for determining the severity of a disease or disorder in a subject, the method comprising administering to said subject at least one glucose analog, imaging the subject's body or region thereof to obtain at least one imaging parameter indicative of the state of the disease or disorder, and comparing said at least one imaging parameter to at least one parameter obtained from said subject at the onset of treatment or prior to treatment commencement, wherein the comparison permits determining the severity of the disease or disorder in the subject.

The invention further provides a method for determining the effectiveness of a therapeutic treatment of a disease or disorder in a subject, the method comprising administering to said subject at least one glucose analog, imaging the subject's body or region thereof to obtain at least one imaging parameter indicative of the state of the disease or disorder, and comparing said at least one imaging parameter to at least one parameter obtained from said subject at the onset of treatment or prior to treatment commencement, wherein the comparison permits determining the effectiveness of the therapeutic treatment of the disease or disorder in the subject.

In some embodiments, the glucose analog is selected amongst $C_1$-$C_5$—O-alkylated glucose and glucose-$C_1$-$C_5$-alkanoates, as defined hereinabove.

In some embodiments, the glucose-$C_1$-$C_5$-alkanoate is 3-O-glucose acetate.

In some embodiments, imaging is by a method selected from nuclear medicine technician, magnetic resonance imaging (MRI), positron emission tomography (PET), radiology (X-ray), ultrasound, computed tomography (CT) and fluorescent imaging.

In some embodiments, the imaging technique is MRI.

In some embodiments, the MRI technique is selected from chemical exchange saturation transfer (CEST) MRI, diffusion MRI, magnetic resonance angiography, dynamic contrast-enhanced MRI (DCE) MRI, and positron emission tomography (PET). In some embodiments, said MRI is chemical exchange saturation transfer (CEST) MRI.

In some embodiments, the disease or disorder is selected amongst disease or disorders involving a high rate of glycolysis in a tissue region as compared to other neighboring or vicinal tissue regions.

In some embodiments, the disease or disorder is selected from proliferative disease or disorders.

In some embodiments, the proliferative disease or disorder is cancer.

In some embodiments, the cancer is selected amongst cancerous states of skin tissues, organs, blood and blood vessels, which include cancers of the bladder, bone, blood, brain, breast, cervix, chest, colon, endrometrium, esophagus, eye, head, kidney, liver, lymph node, lung, mouth, neck, ovary, pancreas, prostate, rectum, stomach, testicles, throat and uterus.

In some embodiments, the cancer is a solid tumor or tumor metastasis.

In some embodiments, the cancer is selected from lung cancer, pancreatic cancers, colon cancers, prostate cancer including the advanced disease, hematopoietic tumors of lymphoid lineage, myeloid leukemias, thyroid follicular cancer, myelodysplastic syndrome (MDS), tumors of mesenchymal origin, melanomas, teratocarcinomas, neuroblastomas, gliomas, glioblastoma, benign tumor of the skin, breast carcinoma, kidney carcinoma, ovary carcinoma, bladder carcinoma and epidermal carcinoma.

In some embodiemnts, the cancer includes advanced malignancy, amyloidosis, neuroblastoma, meningioma, hemangiopericytoma, multiple brain metastase, glioblastoma multiformis, glioblastoma, brain stem glioma, poor prognosis malignant brain tumor, malignant glioma, recurrent malignant glioma, anaplastic astrocytoma, anaplastic oligodendroglioma, neuroendocrine tumor, adenocarcinoma, Dukes C & D colorectal cancer, unresectable colorectal cancer, metastatic hepatocellular carcinoma, Kaposi's sarcoma, karotype acute myeloblastic leukemia, Hodgkin's lymphoma, Non-Hodgkin's lymphoma, cutaneous T-cell lymphoma, cutaneous B-cell lymphoma, diffuse large B-Cell lymphoma, low grade follicular lymphoma, malignant melanoma, malignant mesothelioma, malignant pleural effusion mesothelioma syndrome, intraperitoneal carcinoma, papillary serous carcinoma, gynecologic sarcoma, soft tissue sarcoma, scelroderma, subcutaneous vasculitis, Langerhans' cell histiocytosis, leiomyosarcoma, fibrodysplasia ossificans progressive, hormone refractory prostate cancer, resected high-risk soft tissue sarcoma, unrescectable hepatocellular carcinoma, Waldenstroms macroglobulinemia, smoldering myeloma, indolent myeloma, salpinx cancer, androgen-dependent prostate cancer, androgen-dependent stage IV non-metastatic prostate cancer, hormone-insensitive prostate cancer, chemotherapeutic-insensitive prostate cancer, papillary thyroid carcinoma, follicular thyroid carcinoma, medullary thyroid carcinoma, and leiomyoma, and head and neck cancer.

In some embodiments, the disorder is a wound or atherosclerotic plaques.

In some embodiments, the glucose analog is administered by a route of administration selected from oral, rectal, vaginal, nasal, topical, transdermal and parenteral administration.

In some embodiments, the glucose analog is administered orally as a diagnostically pre-formulated composition.

The invention further provides a kit for diagnostic use, the kit comprising at least one glucose analog or a formulation comprising said analog; and instructions for use. In some embodiments, the analog in the kit is 3OMG.

The invention further provides a diagnostic formulation comprising at least one glucose analogs and at least one diagnostically acceptable carrier, said glucose analog being oxidative phosphorylation inactive.

The formulation is suitable for administration to a subject in preparation for imaging by MRI. In some embodiments, said analog is 3OMG.

The invention further provides use of at least one glucose analog for the preparation of a diagnostic formulation, said glucose analog being oxidative phosphorylation inactive. In some embodiments said analog is 3OMG.

The invention further provides a glucose analog oxidative phosphorylation inactive for use in a method of diagnosis comprising MRI imaging. In some embodiments, the analog is 3OMG.

EXAMPLES

Figure 1:
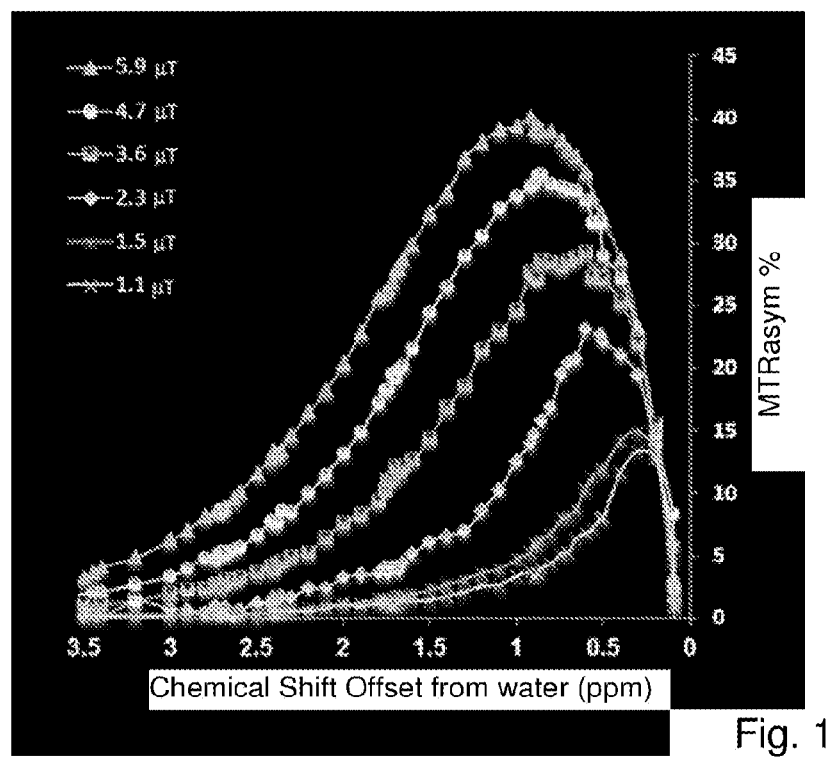
FIG. 1 provides MTRasym plot of 10 mM 3OMG solution (10% $D_2O$) as a function of rf saturation field (B1) at pH=7.5, T=37° C., at 11.7 T.

The following materials were used in the below described examples:
Chemicals and Media: 3OMG, D-glucose, D-glucose 6 phosphate, 2-DG and 2-DG-6P sodium salt were obtained from Sigma-Aldrich, Israel; FDG was obtained from Carbosynth Limited, UK. The glucose analogs were prepared at concentration of 10 mM (pH=7.5), containing 10% $D_2O$ for NMR field locking.

Cells: DA3-D1-DMBA-3 is a cell line derived from a poorly differentiated mammary adenocarcinoma induced in BALB/C mice by dimethylbenzanthracene.

Animals: BALB/C female mice were purchased and kept in the breeding facility of the Sackler School of Medicine, Tel Aviv University. To induce orthotropic tumors in mice, DA3 cells were injected into the lower left mammary gland of 8 week old (17-22 gr) female BALB/c mice (5×105 cells in 100 µL saline). All experiments with animal models were done in compliance with the principles of the National Research Council (NRC) and were approved by the institutional animal care and use committee (IACUC) (# M-12-035).

Preparation of Tumor Extracts: The tumors were surgically excised and weighed quickly and immediately immersed in liquid nitrogen. The frozen tumors were homogenized with a tissue homogenizer, using the methanol/$CHCl_3$/$H_2O$ extraction method 19, a dual-phase extraction procedure to extract intracellular metabolites, with a volume ratio of 2:2:1.8, respectively. After centrifugation (−4° C., 4000×g, 12 min), only the upper aqueous phase was kept for analysis. The samples were dried gently by evaporator, than were frozen at −80° C., and lyophilized to dryness for 24 hr. Each sample was dissolved in 0.5 ml D2O (99.98%, Biolab, Israel), adjusted at pH=6.5-7 and inserted into 5 mm tube for NMR.

NMR Spectroscopy: 1H NMR Spectra were recorded at 500 MHz in 5 mm tubes on a Bruker 500 MHz DRX with the following parameters: spectral width 7500 Hz, pulse width 5.5 us (corresponding to a 45° flip angle); data size 16 K; relaxation delay 10 s; number of scans=16. CEST NMR experiments were performed by applying a long off-resonance presaturation pulse before acquisition. A series of frequencies (Ω) were used in the range of −3.5 to +3.5 ppm relative to the water signal. Several rf saturation field (B1) in the range of 1-6 µT (~50-250 Hz) and durations of 1-4 s were used. The chemical exchange contrast was measured by magnetization transfer asymmetry, MTRasym. CESL NMR experiments were performed by applying a long off-resonance pulse after the hard pulse. A series of frequencies (Ω) were used in the range of −3.5 to +3.5 ppm relative to the water signal. Several rf saturation field (B1) in the range of 1-10 µT (~50-500 Hz) and durations of 10 ms-1 s were used.

CEST MRI experiments were performed on a Bruker 7T Biospec scanner with 30 cm bore size on implanted xenograph mammary tumors of mice before and following the injection of the glucose analog 3OMG. DA3 tumor bearing mice that were allowed to grow for 10-14 days, with an average tumor volume of 5 $mm^3$ were scanned. The mice were anesthetized using isoflurane (1-2%) and scanned with surface coil. Their temperature was monitored and maintained at 37° C. We performed i.p injections of the contrast medium, 3OMG (in saline, pH=7.4).

The In Vivo CEST

Images were generated as follows: a series of gradient-echo images were collected from a single 1 mm axial slice of (acquisition matrix 128×64, field of view of 40×40 mm2) after 1.2 s presaturation pulse of 2.5 µT (106 Hz) at ±1.2 ppm from the water signal. For the MTRasym plot, the mean intensities were used within the selected region of interest (ROI) within the tumor.

In Vitro Studies

Example 1

The magnitude and the frequency dependence of the CEST effect were measured for the glucose analog 3OMG, as potential marker of tumor response. The magnetization transfer asymmetry (MTRasym) plot for 10 mM 3OMG at physiologic parameters (pH=7.5, T=37° C.) is shown FIG. 1. The CEST percent increased with the rf saturation field (B1) and for the peak at 1.2 ppm, reached values of 22% at 3.6 µT (150 Hz).

Example 2

Figure 2:
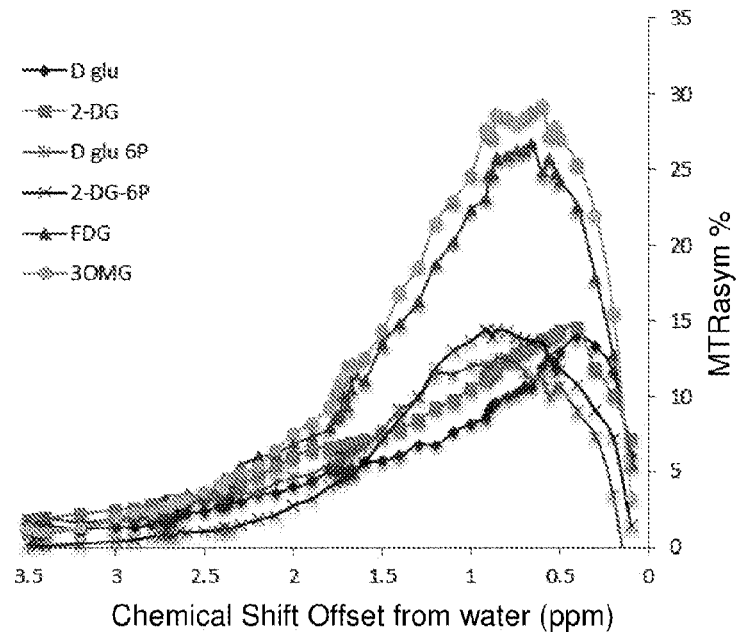
FIG. 2 provides MTRasym plot of 10 mM derivatives of glucose: 2-DG, 2-DG-6P, FDG, D-glu, D-glu-6P and 3OMG (pH=7.5, T=37° C., B1=3.6 µT, at 11.7 T).

The CEST effect obtained for different glucose analogs (under the same conditions) is shown in FIG. 2. It can be noted that the CEST effect is significantly higher for 3OMG solution than the other glucose analogs.

Example 3

Figure 3A:
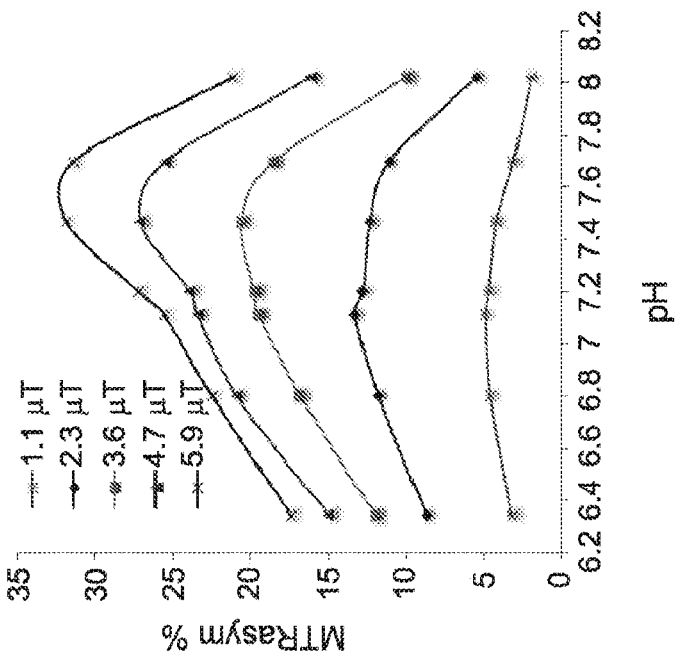
FIGS. 3A-B provide MTRasym plot of a 10 mM 3OMG solution (10% $D_2O$) with pH values from 6.3-7.8 measured (FIG. 3A) at different frequencies offset from water and (FIG. 3B) at frequency offset of 1.2 ppm, as a function of rf saturation field (B1). (T=25° C., at 11.7 T).
Figure 3B:
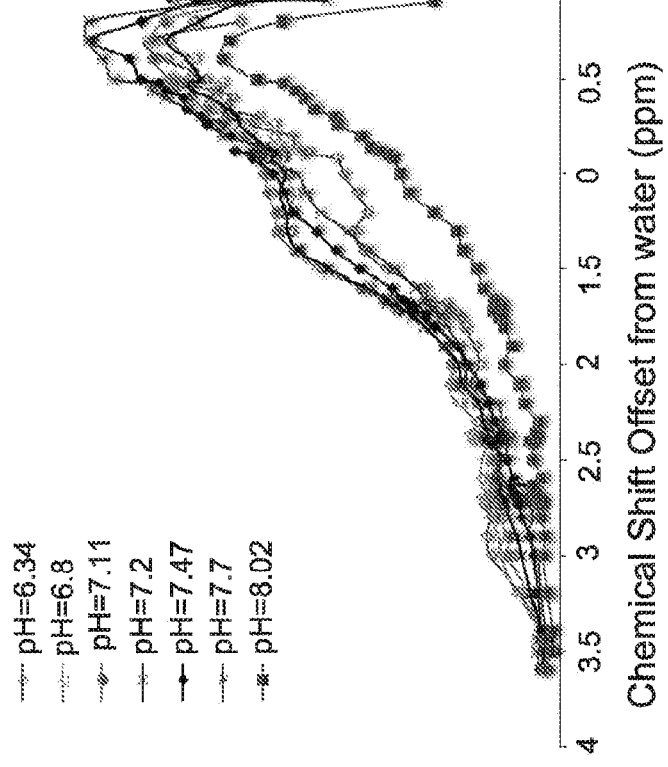

FIG. 3 shows the CEST curves for 10 mM 3OMG solutions at different pH and rf saturation field values. It is interesting to note from FIG. 3A that at the pH range of 7.1-7.5 peaks at 0.3, ~1, 2.1 and 2.7 ppm are clearly resolved for the different OH groups. As can be seen from FIG. 3B, the CEST effect has its maximum around the physiological pH of ~7.5, giving CEST effect of 20-32% for rf saturation field of 3.6-5.9 µT at 11.7 T.

Example 4

Figure 4:
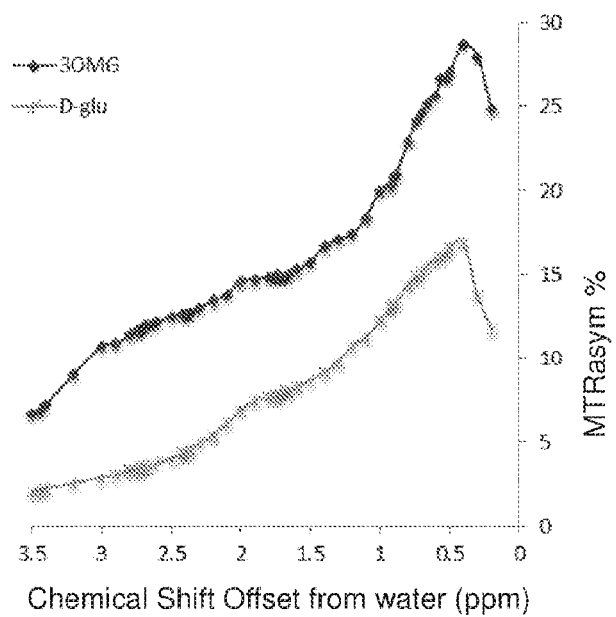
FIG. 4 provides MTRasym plot of combined MCW extracts of tumors treated with 3OMG (blue) and D-glu (red) (B1=2.5 µT, pH=7.0, T=25° C., at 11.7 T).

To evaluate and compare the influence of D-glucose and the glucose analog 3OMG injections on CEST signal, tumors were extracted (by using the methanol-chloroform-water method) from mice after 25 min treatment with 1.5 g/kg D-glucose or 3OMG. The MTRasym plot of the combined extracts of tumors is shown in FIG. 4. As can be seen, the CEST effect for the peak at 1.2 ppm was significantly high for the tumors that were treated with 3OMG compare to those treated with D-glu. Interesting to note the relatively wide frequency range (from 1.5-3 ppm) that yield high CEST signal for the tumors treated with 3OMG compared to those treated with D-glucose. Thus, the measured enhancement in the CEST of the 3OMG extracts, could reflect the potentially tumor uptake of the glucose analog.

Example 5

Figure 5:
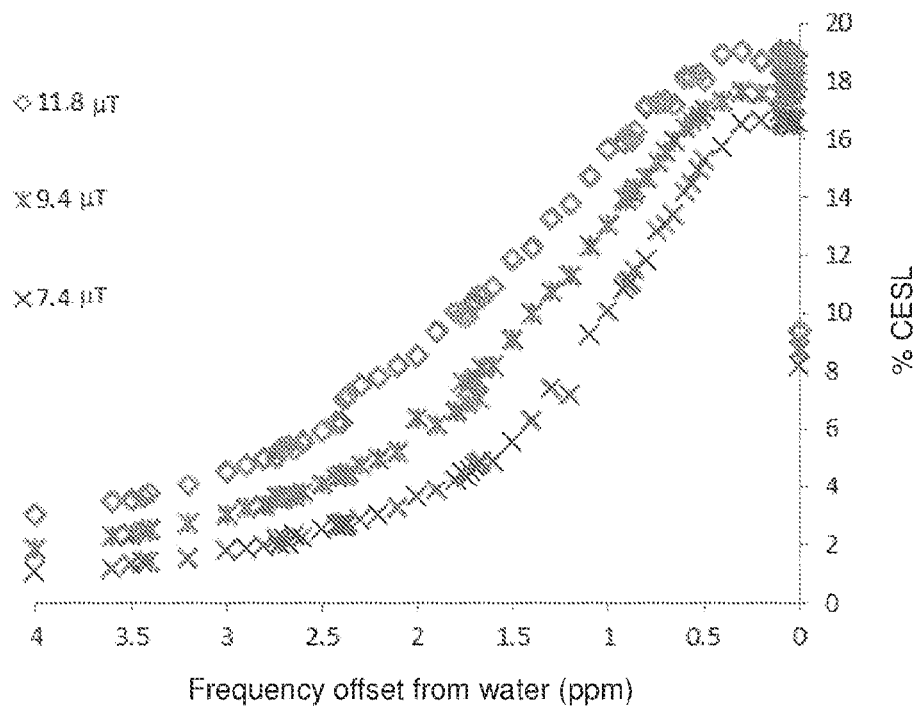
FIG. 5 provides % CESL plot of 10 mM 3OMG solution (10% $D_2O$) as a function of rf saturation field (B1) at pH=7.5, T=37° C., at 11.7 T.
Figure 6A:
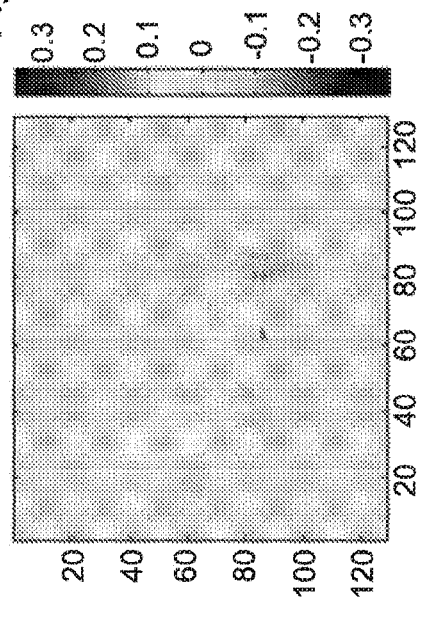
FIGS. 6A-D provide CEST MRI kinetic measurements in the tumor at different times following injection of 3OMG, 1.5 g/kg. The plot describes the results of 5 experiments.
Figure 6B:
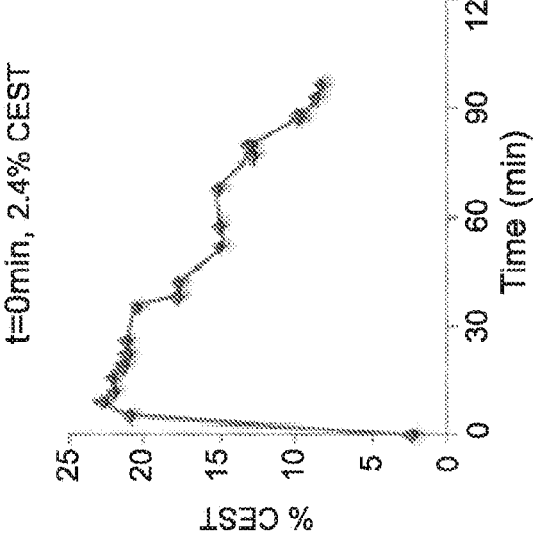
Figure 6C:
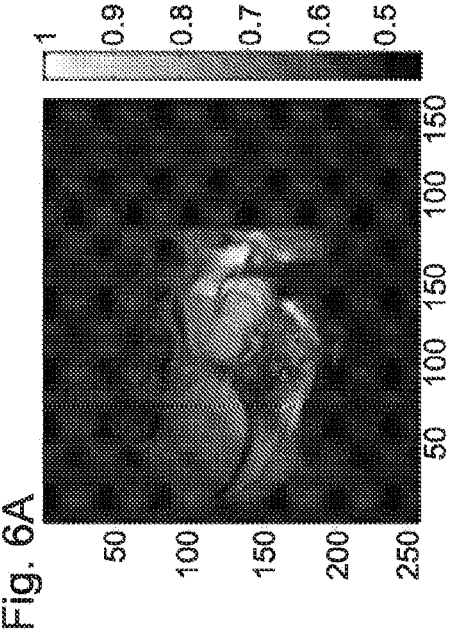
Figure 6D:
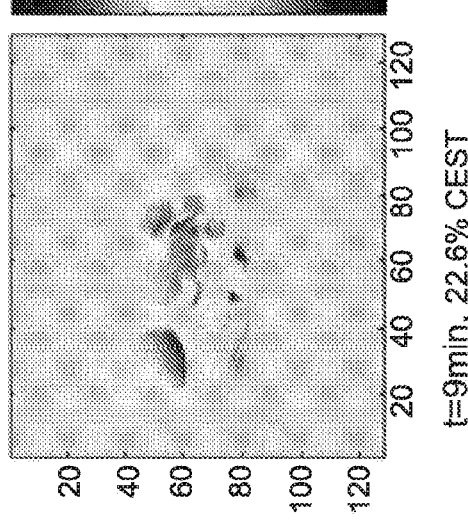

The magnitude and the frequency dependence of the CESL effect were measured for the glucose analog 3OMG as potential marker of tumor response. The magnetization transfer asymmetry (MTRasym) plot for 10 mM 3OMG at physiologic parameters (pH=7.4, T=37° C.) is shown FIG. 5. The CESL percent increased with the rf saturation field (B1) and for the peak at 1.2 ppm, reached values of 14% at 11.8 µT.

In Vivo Studies

Example 6

Having determined in vitro that 3OMG concentrations of only a few millimolar could be detected with CEST method (FIGS. 1-4), the determination of the potential use of 3OMG CEST MRI to image mammary tumors, in vivo, was carried out. Thus performed 3OMG CEST MRI experiments were carried out on mice bearing DA3 tumors injected with 3OMG glucose analog. Tumor anatomy was initially imaged using T2 weighted spin echo sequence (RARE).

As it can be seen from FIGS. 6A-D, within a few min. after the 3OMG injection (1.5 g/kg) a strong and sharp CEST effect was visualized at the tumor. The temporal change in % CEST showed rapid increase of CEST signal of about 20%. Other organs (apart from the urinary bladder) did not show any significant CEST effect throughout the MRI scans session. The signal was slowly declined over more than 1 hour, yet the tumor gave an enhanced CEST MRI image that started to decay only after 20 min.

The 3OMG-CEST MRI was compared to glucoCEST MRI under the same experimental setups. Experiments were carried out using injection of 1.5 g/kg glucose. The two main differences between the glucose experiment and those of the 3OMG glucose analog are the lower (less than 10%) CEST enhancement by the glucose and the sharp decline of the CEST after 20 minutes reaching a value of only 3% above the control, suggesting rapid metabolism. While the CEST of 3OMG last a significant CEST signal for over an hour.

The invention claimed is:

1. A method for imaging at least one body region of a subject, the method comprising administering to said subject an effective amount of at least one non-radio-active labeled glucose analog, and imaging said at least one body region by an imaging method consisting of magnetic resonance imaging (MRI), wherein said at least one glucose analog is a phosphorylation inactive analog selected from methyl-3-O-glucose, ethyl-3-O-glucose, propyl-3-O-glucose, iso-propyl-3-O-glucose, propyl-3-O-glucose, sec-butyl-3-O-glucose, t-butyl-3-O-glucose, n-butyl-3O-glucose and n-pentyl-3-O-glucose, and said MRI is chemical exchange saturation transfer (CEST) MRI solely performed for the imaging.

2. The method according to claim 1, wherein said imaging comprises identifying body regions in which said at least one non-radio-active labeled glucose analog has been localized to identify abnormal tissue.

3. The method according to claim 1 wherein the glucose analogue is 3-O-methylglucose (3OMG).

4. The method according to claim 2, wherein the abnormal tissue has a disease or disorder selected from the group consisting of bladder cancer, bone cancer, blood cancer, brain cancer, breast cancer, cervical cancer, chest cancer, colon cancer, endometrium cancer, esophagus cancer, eye cancer, head cancer, kidney cancer, liver cancer, lymph node cancer, lung cancer, mouth cancer, neck cancer, ovarian cancer, pancreatic cancer, prostate cancer, rectal cancer, stomach cancer, testicular cancer, throat cancer and uterine cancer.

5. The method according to claim 1, wherein said imaging comprises identifying tissue that preferentially takes up the at least one non-radio-active labeled glucose analog as compared to surrounding tissue, said tissue comprising the site of a disease and/or abnormal tissues or organs, wherein the disease and/or abnormal tissues or organs are selected from the group consisting of bladder cancer, bone cancer, blood cancer, brain cancer, breast cancer, cervical cancer, chest cancer, colon cancer, endometrium cancer, esophagus cancer, eye cancer, head cancer, kidney cancer, liver cancer, lymph node cancer, lung cancer, mouth cancer, neck cancer, ovarian cancer, pancreatic cancer, prostate cancer, rectal cancer, stomach cancer, testicular cancer, throat cancer and uterine cancer.

6. The method according to claim 1, wherein said imaging comprises identifying tissue that preferentially takes up the at least one non-radio-active labeled glucose analog, said tissue comprising malignant tumors.

7. The method according to claim 1, wherein said imaging comprises identifying at different time points tissue that preferentially take up the at least one non-radio-active labeled glucose analog, said tissue comprising abnormal tissue.

8. The method according to claim 1, wherein said imaging comprises identifying tissue that preferentially takes up the at least one non-radio-active labeled glucose analog across the at least one body region of a subject, said tissue comprising abnormal tissue, to determine the severity of a disease or disorder in a subject, wherein the disease is selected from the group consisting of bladder cancer, bone cancer, blood cancer, brain cancer, breast cancer, cervical cancer, chest cancer, colon cancer, endrometrium cancer, esophagus cancer, eye cancer, head cancer, kidney cancer, liver cancer, lymph node cancer, lung cancer, mouth cancer, neck cancer, ovarian cancer, pancreatic cancer, prostate cancer, rectal cancer, stomach cancer, testicular cancer, throat cancer and uterine cancer.

9. The method according to claim 1, wherein said imaging comprises identifying at different time points tissue that preferentially takes up the at least one non-radio-active labeled glucose analog to determine the effectiveness of a therapeutic treatment of a disease or disorder in a subject, wherein the disease is selected from the group consisting of bladder cancer, bone cancer, blood cancer, brain cancer, breast cancer, cervical cancer, chest cancer, colon cancer, endrometrium cancer, esophagus cancer, eye cancer, head cancer, kidney cancer, liver cancer, lymph node cancer, lung cancer, mouth cancer, neck cancer, ovarian cancer, pancreatic cancer, prostate cancer, rectal cancer, stomach cancer, testicular cancer, throat cancer and uterine cancer.

10. The method according to claim 2, wherein said imaging comprises imaging for diagnosis of a disease or disorder in a subject, imaging for determining the site of a disease and/or for distinguishing between healthy and abnormal tissues or organs, imaging for distinguishing or differentiating between malignant and benign tumors, imaging for monitoring a disease state in a subject, imaging for determining the severity of a disease or disorder in a subject, or imaging for determining the effectiveness of a therapeutic treatment of a disease or disorder in a subject, wherein the disease or disorder is selected from the group consisting of bladder cancer, bone cancer, blood cancer, brain cancer, breast cancer, cervical cancer, chest cancer, colon cancer, endrometrium cancer, esophagus cancer, eye cancer, head cancer, kidney cancer, liver cancer, lymph node cancer, lung cancer, mouth cancer, neck cancer, ovarian cancer, pancreatic cancer, prostate cancer, rectal cancer, stomach cancer, testicular cancer, throat cancer and uterine cancer.

11. The method according to claim 2, wherein said imaging comprises imaging for diagnosis of a disease or disorder in a subject, imaging for determining the site of a disease and/or for distinguishing between healthy and abnormal tissues or organs, wherein the disease or disorder is selected from the group consisting of bladder cancer, bone cancer, blood cancer, brain cancer, breast cancer, cervical cancer, chest cancer, colon cancer, endrometrium cancer, esophagus cancer, eye cancer, head cancer, kidney cancer, liver cancer, lymph node cancer, lung cancer, mouth cancer, neck cancer, ovarian cancer, pancreatic cancer, prostate cancer, rectal cancer, stomach cancer, testicular cancer, throat cancer and uterine cancer.

12. The method according to claim 2, wherein said imaging comprises imaging for distinguishing or differentiating between malignant and benign tumors, imaging for monitoring a disease state in a subject, wherein the disease is selected from the group consisting of bladder cancer, bone cancer, blood cancer, brain cancer, breast cancer, cervical cancer, chest cancer, colon cancer, endrometrium cancer, esophagus cancer, eye cancer, head cancer, kidney cancer, liver cancer, lymph node cancer, lung cancer, mouth cancer, neck cancer, ovarian cancer, pancreatic cancer, prostate cancer, rectal cancer, stomach cancer, testicular cancer, throat cancer and uterine cancer.

13. The method according to claim 2, wherein said imaging comprises imaging for determining the severity of a disease or disorder in a subject, or imaging for determining the effectiveness of a therapeutic treatment of a disease or disorder in a subject, wherein the disease or disorder is selected from the group consisting of bladder cancer, bone cancer, blood cancer, brain cancer, breast cancer, cervical cancer, chest cancer, colon cancer, endrometrium cancer, esophagus cancer, eye cancer, head cancer, kidney cancer, liver cancer, lymph node cancer, lung cancer, mouth cancer, neck cancer, ovarian cancer, pancreatic cancer, prostate cancer, rectal cancer, stomach cancer, testicular cancer, throat cancer and uterine cancer.

* * * * *